United States Patent [19]

Shimamune et al.

[11] Patent Number: 5,141,576
[45] Date of Patent: * Aug. 25, 1992

[54] TITANIUM COMPOSITE MATERIALS COATED WITH CALCIUM PHOSPHATE COMPOUND AND PROCESS FOR PRODUCTION THEREOF

[75] Inventors: Takayuki Shimamune, Tokyo; Masashi Hosonuma; Yukiei Matsumoto, both of Kanagawa, all of Japan

[73] Assignee: Permelec Electrode, Ltd., Kanagawa, Japan

[*] Notice: The portion of the term of this patent subsequent to Nov. 21, 2006 has been disclaimed.

[21] Appl. No.: 504,457

[22] Filed: Apr. 4, 1990

Related U.S. Application Data

[62] Division of Ser. No. 338,791, Apr. 17, 1989, Pat. No. 4,960,646, which is a division of Ser. No. 29,519, Mar. 24, 1987, Pat. No. 4,882,196.

[30] Foreign Application Priority Data

Mar. 24, 1986 [JP] Japan ............... 61-64012
Mar. 24, 1986 [JP] Japan ............... 61-64013
Mar. 28, 1986 [JP] Japan ............... 61-70504

[51] Int. Cl.⁵ .............................. C23C 22/78
[52] U.S. Cl. .......................... 148/254; 427/2; 148/263
[58] Field of Search ............ 427/2; 148/254, 263

[56] References Cited

U.S. PATENT DOCUMENTS 4,702,930 10/1987 Heide ........................ 427/2
4,882,196 11/1989 Shimamune ............... 427/2

*Primary Examiner*—Sam Silverberg
*Attorney, Agent, or Firm*—Sughrue, Mion, Zinn, Macpeak & Seas

[57] ABSTRACT

A titanium composite material is disclosed which comprises a titanium or titanium alloy substrate, a base layer formed thereon of a calcium phosphate compound resulting from calcination of a hydrochloric or nitric acid aqueous solution of the calcium phosphate compound, and a covering layer thereon of a calcium phosphate compound formed by sintering a suspension of the calcium phosphate compound applied to the base layer. The composite material is useful as a biological implant. It is produced by activating the surface of the substrate, forming the base layer by calcining the solution coated on the substrate and then forming the covering layer by sintering the suspension coated on the base layer. The covering layer may be hydrothermally treated to increase its crystallinity.

7 Claims, No Drawings

TITANIUM COMPOSITE MATERIALS COATED WITH CALCIUM PHOSPHATE COMPOUND AND PROCESS FOR PRODUCTION THEREOF

This is a divisional of application Ser. No. 07/388,791 filed Apr. 17, 1989, now U.S. Pat. No. 4,960,646 which is a divisional of application Ser. No. 07/029,519 filed Mar. 24, 1987, now U.S. Pat. No. 4,882,196.

FIELD OF THE INVENTION

This invention relates to a titanium or titanium alloy composite material coated with a calcium phosphate compound which has especially good affinity for bone or tooth tissues, and a process for production thereof. The titanium or titanium alloy composite material is useful as an implant such as artificial bones, teeth, and tooth roots and a joining material therefor.

BACKGROUND OF THE INVENTION

Biological implants such as artificial bones or tooth roots have recently attracted attention because when bones or teeth are broken or otherwise lost by an accident, etc., the implants can be bonded to the remaining bone or implanted in the bones of the jaw and thus can be used in a form close to natural bones or teeth and ensure maintenance of comfortable daily lives. Since these implants are to be embedded in the body, they should essentially be required to be nontoxic to the body. They are also required to have various other properties, such as sufficient strength, moldability, freedom from dissolution, moderate specific gravity, and biocompatibility.

Metals have been used as biological implants such as artificial bones or tooth roots from the standpoint of their physical strength and workability. Previously, noble metals were used in consideration of effects on the body, but have gradually been replaced by alloys such as stainless steel as a result of development of alloys having good corrosion resistance. Metallic materials containing cobalt as a main component have also been developed and come into use as biological implants.

Among these metallic materials, noble metals are stable, but have the defect of high price, high specific gravity, and high weight. Alloys such as stainless steel have good corrosion resistance, but sometimes contain substances which will cause toxicity when dissolved in vivo. Hence, the alloys are not always versatile, and also have too high a weight as shown by their specific gravity of about 8.

Recently, titanium ($d^{20}=4.50$) or titanium alloys which are nontoxic, stable and light in weight with a relatively low specific gravity came into use.

These metallic materials have sufficient mechanical strength and good workability, but as such, they have the common defect of lacking affinity for bone tissues in vivo.

On the other hand, research has been done on the use of ceramic materials which are stabler and lighter than metals. As a typical material, alpha-alumina is known. This substance is chemically stable, nontoxic, and light and has very high mechanical strength. However, it has the defect that its workability is much inferior to metals, and as such, it lacks affinity with bone tissues. Stabilized zirconia has also come into use because of its good toughness, but has the same defect as alpha-alumina.

As a stable material, a glass material whose surface is mainly rendered porous is also known, but has the defect of insufficient mechanical strength, lack of affinity for the human body, and difficulties in processability.

Recently, apatite ceramics were proposed, which provide a solution to the problem of lack of biocompatibility, which has been a common defect of conventional materials. The main inorganic component of bones or teeth is a calcium phosphate compound (composed mainly of hydroxyapatite), and the apatite ceramics containing this compound as a main component have very good affinity for bones and very good adaptability after being embedded in the body. However, even apatite ceramics which seem to be ideal in some respects have the defects of low mechanical strength, poor moldability, and poor processability, and are limited in use.

In order to overcome these defects, it has been desired to develop metals or ceramic materials having satisfactory biocompatibility by coating apatite on the surface of metals or ceramics. This requires a technique of bonding metal to ceramics or ceramics to ceramics, but the only method now known therefor is plasma spray.

Although the plasma spray method is useful in such bondings, it has the defects that the entire surface of a material having a complex shape is difficult to coat, the entire surface of a porous material cannot be coated, it requires an expensive device, the ratio of utilization of expensive apatite particles is low, and the adhesion between the coating and the substrate is not entirely sufficient.

SUMMARY OF THE INVENTION

It is an object of this invention to provide a material suitable as an implant such as an artificial bone or tooth, which is light, has good workability, and sufficient mechanical strength, does not dissolve in the body, and has enhanced biocompatibility with the body, for example, with bone tissues.

According to this invention, there is first provided a titanium composite material comprising a titanium or titanium alloy substrate, a base layer formed thereon of a calcium phosphate compound resulting from calcination of a hydrochloric or nitric acid aqueous solution of the calcium phosphate compound, and a covering layer thereon of a calcium phosphate compound formed by sintering a suspension of the calcium phosphate compound applied to the base layer.

According to this invention, there is also provided a process for producing a titanium composite material, which comprises activating the surface of a titanium or titanium alloy substrate, coating a hydrochloric or nitric acid aqueous solution of a calcium phosphate compound on the activated surface of the substrate, calcining the coating to form a base layer of the calcium phosphate compound on the substrate, thereafter coating a suspension of a calcium phosphate compound on the base layer, and sintering the coating to form a covering layer of the calcium phosphate compound.

A characteristic feature of the present invention is that in coating calcium phosphate compounds on a titanium or titanium alloy substrate, the base layer obtained by calcination and the coated layer by sintering are laminated.

DETAILED DESCRIPTION OF THE INVENTION

The present invention is now described below in more detail.

The present invention provides a titanium composite material composed of a titanium or titanium alloy substrate and layers of calcium phosphate compounds coated thereon, which is suitable as an implant such as an artificial bone or tooth roots; and a process for production thereof.

The calcium phosphate compound, as used herein, generically denotes tricalcium phosphate, calcium hydrogen phosphate, calcium dihydrogen phosphate, and apatite-type compounds which are phosphate salts of calcium containing fluorine, chlorine, or a hydroxyl group, typified by hydroxyapatite (calcium hydroxyphosphate). In the present invention, these compounds, as such or containing other biologically nontoxic compounds or impurities, may be properly used as the base layer and the covering layer. By providing a coating of the calcium phosphate compound on the surface of titanium or a titanium alloy, the material provided by this invention can be joined to bones, etc. in the body with sufficiently high biocompatibility.

The titanium or the titanium alloy used as the substrate in this invention may be selected from metallic titanium and titanium alloys of titanium with Ta, Nb, platinum-group metals, Al, V, etc. The substrate may be in the form of a plate, a rod, etc. having a smooth surface or a spongy porous surface. The use of titanium or the titanium alloy as the substrate is due to the fact that it is nontoxic and stable in the body, has a specific gravity about 60% of that of an alloy which dissolves (such as stainless steel), and that it has sufficiently high mechanical strength and is easy to work. The affinity of the substrate for the calcium phosphate compound may be increased by subjecting its surface to a cleaning treatment such as washing with water, pickling, ultrasonic cleaning, or vapor cleaning, thus removing impurities. As required, the surface of the substrate may be roughened by blasting and/or etching thereby to increase its affinity for the calcium phosphate compound and at the same time activate it. The etching can be carried out not only chemically, but also physically by, for example, sputtering.

A hydrochloric or nitric acid aqueous solution of the calcium phosphate compound is coated on the surface of the substrate and calcined by heating to form a base layer of the calcium phosphate compound firmly bonded to the titanium or the titanium alloy of the substrate. At this time, it is desirable to form a uniform aqueous solution of a calcium phosphate compound having a high solubility such as calcium hydrogen phosphate or calcium dihydrogen phosphate. In the present invention, titanium and/or tin and/or a compound of such a metal may be included in the aforesaid hydrochloric or nitric acid aqueous solution. Titanium or tin or compounds of these may be a metallic element or a compound if they dissolve in hydrochloric acid or nitric acid and generate titanium oxide or tin oxide by being calcined. Examples of the compounds are inorganic salts typified by halogen compounds such as titanium (II) chloride, titanium (III) chloride, stannous chloride, and stannic chloride, organic salts such as tin oxalate, and organometallic compounds such as n-butyl titanate or alkoxytins. Titanium oxide and tin oxide themselves are also included within their examples.

Since in the present invention, a solution of the calcium phosphate compound is coated on the substrate and the compound is then precipitated from the solution by heating, a uniform coating can be formed entirely on the surface irrespective of the form of substrate, for example, even on a substrate having a porous surface. The reason for using the aqueous hydrochloric or nitric acid solution for dissolving the calcium phosphate compound is that the calcium phosphate compound can be easily dissolved in it and that the titanium or titanium alloy as the substrate is partly dissolved at the time of calcination and forms a chemical bond with the calcium phosphate compound to form a firmly adherent calcium phosphate coating.

When the aforesaid coating is calcined, the calcium phosphate compound precipitates mainly as hydroxyapatite or tricalcium phosphate on the substrate. The calcination temperature at this time is from 200° to 800° C. If the temperature is below 200° C., the calcination does not sufficiently proceed, and the resulting coating does not sufficiently adhere to the substrate. If it is higher than 800° C., surface oxidation of the titanium or titanium alloy substrate becomes predominant and the adhesion of the base layer of the calcium phosphate compound to the substrate is reduced. If titanium or tin or a compound of such a metal is dissolved in the aqueous hydrochloric or nitric acid solution, titanium oxide and/or tin oxide precipitates as a base layer together with the calcium phosphate compound. If titanium oxide or tin oxide is included in the base layer, it forms a very firm bondage with titanium or the titanium alloy as the substrate to bond the base layer more firmly to the substrate. Titanium oxide and tin oxide are very stable chemically and do not undergo a chemical change in the body. Hence, no toxic substance dissolves from them, nor does the coating of the base layer become brittle or weakened. The amount of titanium oxide and/or tin oxide to be included in the base layer can be properly selected; preferably the amount is not more than 80% by weight.

On the surface of the base layer, a covering layer of the calcium phosphate compound is laminated to a required thickness. The calcium phosphate compound of the covering layer may be the same as, or different from, the calcium phosphate compound of the base layer. Formation of this covering layer can be easily performed by an ordinary sintering method, since the covering layer is formed on a base layer of the calcium phosphate coating strongly bonded to the substrate.

A suspension of the desired calcium phosphate compound is coated on the substrate having the thin base layer of the calcium phosphate compound. The concentration of the suspension can be freely selected according to the required thickness of the covering layer. After drying, the applied coating is sintered, desirably at a temperature of from 300° to 900° C. If it is less than 300° C., the sintering does not proceed. If it is above 900° C., it is likely to exceed the alpha-beta transition point of titanium, and there is a possibility of adverse effects on the substrate. The sintering temperature and time are determined according to the state and thickness of the calcium phosphate compound. If the temperature is high, tricalcium phosphate becomes predominant. If it is relatively low, hydroxyapatite becomes predominant.

One reason for using the suspension in forming the covering layer is to roughen the surface of the resulting covering layer, and thus increase the resistance of the coated layer to detachment and to increase its affinity for bone tissues in vivo.

As required, both the base layer and the covering layer may be formed in desired thicknesses by repeating the above operations.

The reason for laminating both the base layer of the calcium phosphate compound and the covering layer of the calcium phosphate compound to the titanium or titanium alloy substrate is to provide a titanium composite material having high affinity for the substrate and sufficiently high strength. This is accomplished by forming the base layer of the calcium phosphate compound which has relatively low mechanical strength but is uniform and has high affinity for the entire surface of the titanium or titanium alloy substrate by calcination, coating a calcium phosphate compound having identical or similar properties to the base layer on the base layer to impart a firm bondage between the base layer and the coated layer, thus forming the calcium phosphate compound having high strength. If a single coated layer of the calcium phosphate compound is formed on the substrate by sintering, the strength of the coated layer is high, but its affinity for the substrate is low and it is liable to peel off from the substrate. Such a composite material is not, of course, useful as an implant.

The above process can give a titanium composite material having a calcium phosphate compound coating with biocompatibility. The calcium phosphate compound of the coated layer formed by sintering has a low crystallinity or is close to an amorphous compound. It is especially preferred to perform a hydrothermal treatment in order to increase the crystallinity and the strength of the above compound and improve its biocompatibility.

The hydrothermal treatment denotes a crystal growth method carried out in the process of water at high temperatures, particularly water at high temperatures and pressures.

The hydrothermal treatment conditions are not particularly limited. Desirably, the hydrothermal treatment is carried out in an autoclave at a temperature of from 100° to 200° C. (under a pressure of about from 1 to 16 kg/cm$^2$) in the presence of steam. This results in an increase in the crystallinity of the covering layer. By this hydrothermal treatment, part of the tricalcium phosphate is converted to hydroxyapatite.

Generally, crystals of hydroxyapatite are produced at from 400° to 500° C. In the above-described preferred embodiment, the hydrothermal treatment is carried out under the above relatively mild conditions, since it is for the purpose of increasing the crystallinity and stability of the covering layer. Treatment at higher temperatures is not necessary. Of course, the treatment may be carried out at temperatures of from 200° C. to 500° C. without consideration of economy, and in this case, the quality of the product is not degraded.

The following Examples illustrate the present invention more specifically. It should be understood, however, that these examples do not in any way limit the present invention.

EXAMPLE 1

Calcium hydrogen phosphate (CaHPO$_4$) was dissolved in a 20% aqueous solution of nitric acid to prepare a coating solution containing 10% of calcium hydrogen phosphate.

The surface of a titanium substrate having a length of 10 cm, a width of 10 cm, and a thickness of 3 mm was roughened by blasting it with a steel grit (average particle diameter 0.8 mm), and then etched in a 15% aqueous solution of oxalic acid at 95° C. for 6 hours.

The above coating solution was coated on the activated titanium substrate, dried at 80° C. for 20 minutes, and subsequently calcined at 500° C. for 30 minutes.

The operation from the coating to the calcination was repeated twice to form a firm base layer of tricalcium phosphate having a thickness of about 2 micrometers on the surface of the titanium substrate. Analysis by an electron probe microanalyzer (produced by Hitachi Ltd.) showed the presence of about 10% of titanium in the base layer in addition to tricalcium phosphate.

A suspension was prepared by pulverizing a powder of tricalcium phosphate reagent (special grade) in an agate mortar for 10 hours and dispersing the pulverized powder in a 5% aqueous solution of hydrochloric acid, and coated on the titanium substrate having the base layer of tricalcium phosphate. The coated titanium substrate was dried at 80° C. for 1 hour, and sintered at 700° C. for 3 hours. This operation was repeated twice to form a firm uniform sintered covering layer composed mainly of tricalcium phosphate having a thickness of about 100 micrometers.

EXAMPLE 2

Calcium hydrogen phosphate was dissolved in a 20% aqueous solution of hydrochloric acid to form a coating solution containing 5% of calcium hydrogen phosphate. The solution was coated by a brush on a titanium substrate prepared as in Example 1, dried at 80° C. for 20 minutes and calcined for 20 minutes in an argon atmosphere containing 10% (by volume) oxygen at 600° C. This operation was repeated three times to form a firm base layer composed of tricalcium phosphate and having a thickness of about 2 micrometers on the titanium substrate.

Analysis by an electron probe microanalyzer as in Example 1 showed that the base layer contained 25% titanium, which seemed to have been derived from the titanium substrate.

A suspension was prepared by dissolving calcium hydroxide in a 10% aqueous solution of nitric acid, adding calcium hydrogen phosphate so as to provide a Ca$^{2+}$ ion to PO$_4^{3-}$ ion mole ratio of 3/2, and further adding the same tricalcium phosphate powder as used in Example 1. The suspension was coated on the base layer, dried at 80° C. for 1 hour and then sintered in an argon atmosphere at 800° C. for 2 hours. As a result, a titanium plate having a very firm covering layer of calcium phosphate with a thickness of about 50 micrometers was obtained.

When sintering of the coating from the suspension was carried out at 950° C. for 1 hour, marked grain growth of titanium, presumably due to titanium transition, was observed, and the coating partly peeled off.

EXAMPLE 3

A base layer of calcium phosphate was formed in the same way as in Example 2 on a titanium substrate treated as in Example 1. For comparison, a bare titanium substrate without this base layer was prepared.

A suspension of calcium phosphate compound containing hydroxyapatite as a main component was coated on each of these substrates, dried at 80° C. for 1 hour, and then, sintered at 800° C. for 2 hours in an argon atmosphere.

The above suspension had been prepared by dissolving calcium hydroxide in a 10% aqueous solution of nitric acid, adding calcium hydrogen phosphate so that the mole ratio of a $Ca^{2+}$ ion and $PO_4^{3-}$ ion became 5/3, and further adding a fine powder of hydroxyapatite obtained by pulverization in an agate mortar for 10 hours.

In the titanium substrate on which the base layer of calcium hydrogen phosphate was formed and the covering layer from the suspension was formed by sintering, a firm coating of hydroxyapatite having a thickness of about 50 micrometers was seen to form. In the titanium substrate having no base layer of calcium hydrogen phosphate, a coating of hydroxyapatite could likewise be formed. But this coating was so weak as to be easily peeled by a tape test. The tape test is a test by which an adhesive tape such as a Scotch tape is applied to the surface of the coating, and then peeled from it at an angle of 90° to determine whether the coating adheres to the peeled tape. If the coating has a weak strength, it will be peeled while adhering to the tape.

EXAMPLE 4

The surface of a titanium substrate having a length of 10 cm, a width of 10 cm, and a thickness of 3 mm was roughened by blasting it with a stainless steel cut wire (diameter 0.8 mm), and then subjected to pickling in a 20% aqueous solution of hydrochloric acid at 60° C. to remove matter adhering to the surface.

A coating solution was prepared by dissolving calcium hydrogen phosphate in an aqueous solution of hydrochloric acid containing titanium (III) chloride (5 g/liter of titanium) so that the calcium content became 5 g/liter. The coating solution was coated on the titanium substrate, dried at 80° C. for 15 minutes, and subsequently calcined in a current of air at 500° C. for 15 minutes. This operation was repeated four times to form a firm base layer having a thickness of about 1 to 2 micrometers and composed of a mixture of titanium oxide and tricalcium phosphate.

A suspension prepared by pulverizing a powder of tricalcium phosphate reagent (Special Grade) in an agate mortar for 10 hours and then dispersing the pulverized powder in a 5% aqueous solution of hydrochloric acid was coated on the titanium substrate having the coating of a mixture of tricalcium phosphate and titanium oxide.

The coated titanium substrate was dried at 80° C. for 1 hour and further heated in argon gas at 900° C. for 1 hour. This operation was repeated twice to form a titanium substrate having a uniform and firm covering layer of calcium phosphate with a thickness of about 50 micrometers.

For comparison, the base layer was not formed, but the suspension of calcium phosphate was directly coated on the pre-treated titanium substrate and heat-treated under the same conditions. This operation was repeated twice. A coating of tricalcium phosphate having a thickness of about 50 micrometers could be formed. But its physical strength was insufficient, and by lightly tapping it with a hammer, cracking and peeling occurred.

EXAMPLE 5

A titanium substrate was prepared as in Example 4.

Calcium hydrogen phosphate and tin oxalate were dissolved in a 20% aqueous solution of nitric acid to prepare a coating solution containing calcium and tin each in a concentration of 5 g/liter. The coating solution was coated on the titanium substrate, dried at 150° C. for 10 minutes, and subsequently calcined at 520° C. for 15 minutes. This operation was repeated six times to form a firm base layer having a thickness of about 1 to 2 micrometers and composed of a mixture of tin oxide and calcium phosphate compound.

A suspension was prepared by dissolving calcium hydroxide ($Ca(OH)_2$) in a 10% aqueous solution of nitric acid, adding calcium hydrogen phosphate ($CaHPO_4$) so that the mole ratio of a $Ca^{2+}$ ion to a $PO_4^{3-}$ ion became 3/2, and further adding a fine powder of tricalcium phosphate. The suspension was then coated further on the titanium substrate having the base layer, dried at 80° C. for 1 hour, and then sintered in air at 750° C. for 3 hours. This operation was repeated twice to form a titanium substrate having a firm and uniform covering layer of calcium phosphate compound with a thickness of about 100 micrometers.

EXAMPLE 6

A coating solution containing 2 g/liter of titanium, 3 g/liter of tin, and 5 g/liter of calcium was prepared by dissolving stannous chloride in amyl alcohol, refluxing the solution to form alkoxytin, adding a small amount of water, allowing the mixture to stand, adding a hydrochloric acid aqueous solution of titanium (III) chloride, and further dissolving calcium hydrogen phosphate.

The coating solution was coated on a titanium substrate treated as in Example 4, dried at room temperature and at 180° C. for 20 minutes, and calcined at 480° C. for 20 minutes. This operation was repeated six times to form a base layer having a thickness of 1 to 2 micrometers and composed of titanium oxide, tin oxide, and calcium phosphate compound.

The same suspension as in Example 4 was coated further on the resulting substrate having the base layer, dried at 80° C. for 1 hour, and then sintered in an argon gas at 850° C. for 1 hour. This operation was repeated twice to form a titanium substrate having a firm and uniform covering layer of calcium phosphate compound with a thickness of about 50 micrometers.

For comparison, the suspension coated was sintered at 950° C. (above the transition point of titanium). A firm coating was obtained, but the crystal grains of the titanium substrate became rather large. This does not seem to be any significant problem in ordinary use. It is anticipated, however, that problems will occur if it is used for a long period of time at a part on which a special force may be exerted.

EXAMPLE 7

The same coating solution as used in Example 4 (a hydrochloric acid aqueous solution of titanium (III) chloride and calcium hydrogen phosphate) was coated on a titanium substrate composed of an alloy of Ti-6% Al-4% V treated as in Example 4 and calcined under the same conditions to form a coating. Then, the same coating solution as used in Example 5 (a nitric acid aqueous solution of tin oxalate and calcium hydrogen phosphate) was coated on it and calcined under the same conditions as in Example 4. These operations were each repeated four times to form a coating of titanium-calcium phosphate and a coating of tin-calcium phosphate alternately. As a result, a firm base layer having a thickness of 2 to 3 micrometers and substantially composed of a mixture of titanium oxide, tin oxide, and calcium phosphate was obtained.

A suspension of hydroxyapatite was prepared by dissolving calcium hydroxide ($Ca(OH)_2$) in a 10% aqueous solution of nitric acid, adding calcium hydrogen phosphate $CaHPO_4$) so that the mole ratio of a $Ca^{2+}$ ion to a $PO_4^{3-}$ ion became 5/3, and further adding hydroxyapatite finely pulverized for 10 hours in an agate mortar. The suspension was coated on the base layer, dried at 80° C. for 1 hour, and then, sintered at 800° C. for 2 hours in an argon atmosphere.

EXAMPLE 8

The X-ray diffraction of the crystalline phase of the coated layer obtained as in Example 1 showed that it was composed of tricalcium phosphate having a low crystallinity, i.e., nearly amorphous tricalcium phosphate.

The titanium substrate having the composite layer formed thereon was put in a stainless steel autoclave together with pure water, and hydrothermally treated at each of the temperatures indicated in Table 1 for each of the times indicated in Table 1. The results are shown in Table 1.

As shown in Table 1, there was no change after the treatment at 90° C. At 100° C. or above, there was a growth of crystals, and at higher temperatures, conversion of tricalcium phosphate to hydroxyapatite was observed.

TABLE 1

| Treating temperature (°C.) | Treating time (hours) | Crystalline phase of the coated layer |
|---|---|---|
| — | — | Nearly amorphous tricalcium phosphate |
| 90 | 2 | Nearly amorphous tricalcium phosphate |
| 110 | 2 | Crystalline tricalcium phosphate and hydroxyapatite |
| 150 | 2 | Crystalline hydroxyapatite and a tiny amount of tricalcium phosphate |
| 190 | 2 | Crystalline hydroxyapatite |

EXAMPLE 9

A firm base layer composed of a mixture of titanium oxide and tricalcium phosphate was formed on a titanium substrate in the same way as in Example 4.

A suspension was prepared by dissolving calcium hydroxide in a 10% aqueous solution of nitric acid, adding calcium hydrogen phosphate so that the mole ratio of a $Ca^{2+}$ ion to a $PO_4^{3-}$ ion became 3/2, and adding the same tricalcium phosphate powder as in Example 1. The suspension was coated on the base layer, dried at 80° C. for 1 hour, and then sintered in an argon atmosphere at 800° C. for 2 hours.

As a result, a titanium plate having a very firm covering layer of calcium phosphate compound with a thickness of about 50 micrometers was obtained.

The coated titanium plate was hydrothermally treated in an autoclave in the presence of steam at 180° C. for 3 hours. As a result, a greater part of the calcium phosphate compound in the covering layer was converted to hydroxyapatite, and a titanium plate having a hydroxyapatite coating having good crystallinity was obtained.

EXAMPLE 10

A urethane foam was impregnated with a suspension of fine titanium particles and subjected to sintering in an inert atmosphere to obtain a three-dimensional network structure of titanium having a porosity of from 90 to 95%.

This structure was used as a substrate and surface-activated by etching in a 15% aqueous solution of hydrochloric acid at 80° C. A base layer and a covering layer of calcium phosphate compounds were formed on the surface of the substrate under the same conditions as in Example 1, except that the coating was carried out by dipping instead of the brush method. As a result, a three-dimensional network titanium composite material was obtained having a composite coating having a thickness of about 50 micrometers and composed of the base and covering layers of calcium phosphate compounds.

The composite material was hydrothermally treated in a stainless steel autoclave at 150° C. for 4 hours. As a result of this treatment, the calcium phosphate compound close to an amorphous compound was converted to a mixture of tricalcium phosphate and hydroxyapatite having relatively good crystallinity.

There are several major advantages of this invention.

Firstly, using titanium or a titanium alloy as a substrate, an artificial bone or tooth root made from the resulting composite material is nontoxic to the body, and is unlikely to dissolve out. The composite material is light in weight and has sufficiently high mechanical strength. It is also very easy to work.

Secondly, since the calcium phosphate compound is coated on the surface of the titanium or titanium alloy substrate, the resulting composite material has sufficiently high biocompatibility and can be joined easily with sufficient strength.

Thirdly, since the composite coating is formed by first forming a base layer of the calcium compound on the surface of the substrate by calcination, and then forming a covering layer of calcium phosphate compound on it by sintering, there is very high affinity between the substrate and the base layer and between the base layer and the covering layer. Furthermore, since the surface layer is formed by sintering and has high strength, the entire composite material has high strength.

Fourthly, since in the formation of the base layer, a solution of the calcium phosphate compound is coated on the substrate and the calcium phosphate compound is precipitated from the solution, a uniform coating can be formed throughout the surface of a substrate of any shape. Further, the ratio of utilization of the calcium phosphate compound is good, and a coating of good quality can be formed by easily controlling the state of the coating.

Fifthly, the coated layer of the calcium phosphate compound formed by sintering and having a relatively low crystallinity is hydrothermally treated to increase its crystallinity. Hence, the strength of the coated layer itself is increased and the biocompatibility of the resulting composite material is also increased. Consequently, the function of the composite material as a biological implant is strikingly enhanced.

While the invention has been described in detail and with reference to specific embodiments thereof, it will be apparent to one skilled in the art that various changes and modifications can be made therein without departing from the spirit and scope thereof.

What is claimed is:

1. A process for producing a titanium composite material, which comprises activating the surface of a titanium or titanium alloy substrate, coating a hydrochloric or nitric acid aqueous solution of a calcium phosphate compound on the activated surface of the substrate, calcining the coating to form a base layer of the calcium phosphate compound on the substrate, thereafter coating a suspension of a calcium phosphate compound on the base layer, and sintering the coating to form a covering layer of the calcium phosphate compound.

2. A process for producing a titanium composite material as in claim 1, wherein the calcium phosphate compound formed as the base layer and the covering layer is mainly at least one of hydroxyapatite and tricalcium phosphate.

3. A process for producing a titanium composite material as in claim 1, wherein the activation of the surface of said substrate is carried out by at least one of blasting and etching.

4. A process for producing a titanium composite material as in claim 1, wherein the calcination is carried out at a temperature of from 200° to 800° C.

5. A process for producing a titanium composite material as in claim 1, wherein the sintering is carried out at a temperature of from 300° to 900° C.

6. A process for producing a titanium composite material as in claim 1, wherein the covering layer is then hydrothermally treated.

7. A process for producing a titanium composite material as in claim 12, wherein the hydrothermal treatment is carried out in steam at a temperature of from 100° to 200° C.

* * * * *